(12) United States Patent
Bergström et al.

(10) Patent No.: US 11,519,834 B2
(45) Date of Patent: Dec. 6, 2022

(54) IN VITRO INTESTINAL DRUG DISPOSITION DEVICE

(71) Applicant: Enphasys AB, Knivsta (SE)

(72) Inventors: Christel Bergström, Knivsta (SE); Janneke Keemink, Uppsala (SE)

(73) Assignee: Enphasys AB, Knivsta (SE)

( * ) Notice: Subject to any disclaimer, the term of this patent is extended or adjusted under 35 U.S.C. 154(b) by 382 days.

(21) Appl. No.: 16/642,319

(22) PCT Filed: Jul. 9, 2018

(86) PCT No.: PCT/SE2018/050752
§ 371 (c)(1),
(2) Date: Feb. 26, 2020

(87) PCT Pub. No.: WO2019/045615
PCT Pub. Date: Mar. 7, 2019

(65) Prior Publication Data
US 2021/0072126 A1    Mar. 11, 2021

(30) Foreign Application Priority Data

Sep. 4, 2017 (SE) .................................... 1751066-0

(51) Int. Cl.
*G01N 33/15* (2006.01)
*G01N 1/40* (2006.01)
(Continued)

(52) U.S. Cl.
CPC .......... *G01N 1/4005* (2013.01); *G01N 1/405* (2013.01); *G01N 33/15* (2013.01); *G01N 33/92* (2013.01);
(Continued)

(58) Field of Classification Search
CPC ...... G01N 1/4005; G01N 1/405; G01N 33/15; G01N 33/92; G01N 2001/002; G01N 2001/4016
(Continued)

(56) References Cited

U.S. PATENT DOCUMENTS 4,681,858 A * 7/1987 Chaudhari ............ B01F 21/221
73/866
2008/0223116 A1* 9/2008 Alkhawam ............ G01N 33/15
73/866

FOREIGN PATENT DOCUMENTS

WO    2017085189    *  5/2017

OTHER PUBLICATIONS

Di Cagno, M. et al., "New Biomimetic Barrier Permeapad(TM) for Efficient Investigation of Passive Permeability of Drugs," Eur. J. Pharm. Sci. 73(20):29-34 (2015).
(Continued)

*Primary Examiner* — Robert R Raevis
(74) *Attorney, Agent, or Firm* — Law Offices of Nisan Steinberg

(57) ABSTRACT

An in vitro intestinal drug disposition device (1) comprises a donor chamber (2) for a donor solution and having a bottom end (18) and a top end (19). The device (1) also comprises a receiver chamber (3) for an absorption solution and an absorption membrane (4) arranged in between and separating the chambers (2, 3). A first side (5) of the absorption membrane (4) is to be in contact with the donor solution and a second side (6) of the absorption membrane (4) is to be in contact with the absorption solution. A ratio of an internal volume of the donor chamber (2) to an area of the first membrane side (5) is equal to or smaller than 3 ml/cm$^2$. A cross-sectional area of the donor chamber (2) at (Continued)

the bottom end (18) is larger than a cross-sectional area of the donor chamber (2) at the top end (19).

14 Claims, 9 Drawing Sheets

(51) Int. Cl.
*G01N 33/92* (2006.01)
*G01N 1/00* (2006.01)
(52) U.S. Cl.
CPC .............. *G01N 2001/002* (2013.01); *G01N 2001/4016* (2013.01)
(58) Field of Classification Search
USPC .. 73/863.23, 61.3, 159, 865.6, 865.8, 865.9; 434/262, 267, 268, 227
See application file for complete search history.

(56) References Cited

OTHER PUBLICATIONS

Crum, M.F. et al., "A new in vitro lipid digestion—in vivo absorption model to evaluate the mechanisms of drug absorption from lipid-based formulations," Pharm. Res. 33:970-982 (2016).
Dahan, A. et al., "The Effect of Different Lipid Based Formulations on the Oral Absorption of Lipophilic Drugs: The Ability of in Vitro Lipolysis and Consecutive Ex Vivo Intestinal Permeability Data to Predict in Vivo Bioavailability in Rats," Eur. J. Pharm. Biopharm. 67(1):96-105 (2007).
Heikkinen, A.T. et al., "Modelling of drug disposition kinetics in in vitro intestinal absorption cell models," Basic Clin. Pharmacol. Toxicol. 106(3):180-188 (2010).
Hubatsch, I. et al., "Determination of drug permeability and prediction of drug absorption in Caco-2 monolayers," Nature Protocols 2(9):2111-2119 (2007).
Jain, A.S. et al., "In Vitro and Ex Vivo Evaluations of Lipid Anti-Cancer Nanoformulations: Insights and Assessment of Bioavailability Enhancement," AAPS PharmSciTech, 17(3):553-571 (2016).
Kataoka, M. et al., "In Vitro System to Evaluate Oral Absorption of Poorly Water-Soluble Drugs: Simultaneous Analysis on Dissolution and Permeation of Drugs," Pharm. Res., 20(10):1674-1680 (2003).
Lundquist, P., et al., "Oral absorption of peptides and nanoparticles across the human intestine: Opportunities, limitations and studies in human tissues," Advanced Drug Delivery Reviews, vol. 106, Part B, pp. 256-276 (2016).
Mols, R. et al., "Sulfasalazine transport in in-vitro, ex-vivo and in-vivo absorption models: contribution of efflux carriers and their modulation by co-administration of synthetic nature-identical fruit extracts," J. Pharm. Pharmacol. 57:1565-1573 (2005).
Mudie, D. M. et al., "Mechanistic Analysis of Solute Transport in an in Vitro Physiological Two-Phase Dissolution Apparatus," Biopharm Drug Dispos. 33(7):378-402 (2012).
Nunes, R. et al., "Tissue-based in vitro and ex vivo models for intestinal permeability studies," Chapter 4.2 IN: Sarmento, Bruno, Ed., Concepts and Models for Drug Permeability Studies, 1st Edition, ISBN: 9780081000946, Woodhead Publishing (Elsevier), pp. 203-236 (Oct. 1, 2015).
Stillhart, C. et al., "Biopharmaceutical Modeling of Drug Supersaturation During Lipid-Based Formulation Digestion Considering an Absorption Sink," Pharm. Res. 31:3426-3444 (2014).
Tanojo, H. et al., "New design of a flow-through permeation cell for studying in vitro permeation studies across biological membranes," J. Controlled Release 45:41-47 (1997).
Tsinman, K. et al., "In Situ Method for Monitoring Free Drug Concentration Released from Nanoparticles," American Association of Pharmaceutical Scientists (AAPS) Annual Meeting 2013, San Antonio, TX (Abstract Only).
Tsinman, K. et al., "In Situ Method for Monitoring Free Drug Concentration Released from Nanoparticles," American Association of Pharmaceutical Scientists (AAPS) Annual Meeting 2013, San Antonio, TX (Poster).
Williams, H.D. et al., "Toward the Establishment of Standardized In Vitro Tests for Lipid-Based Formulations, Part 1: Method Parameterization and Comparison of In Vitro Digestion Profiles Across a Range of Representative Formulations," J. Pharm. Sci. 101(9):3360-3380 (2012).
Wilson, G. et al., "Transport and permeability properties of human Caco-2 cells: An in vitro model of the intestinal epithelial cell barrier," J. Controlled Release 11:25-40 (1990).
EPO Communication under Rule 161 &162 EPC in EP18743606.8 (European phase of PCT/SE2018/050752), dated Apr. 16, 2020.
International Preliminary Report on Patentability (IPRP) in PCT/SE2018/050752, dated Mar. 10, 2020.
Written Opinion and International Search Report (ISR) of ISA/EP in PCT/SE2018/050752, dated Dec. 5, 2018.
Written Opinion and International Search Report (ISR) of ISA/EP in PCT/SE2018/050752, dated Sep. 17, 2018.

* cited by examiner

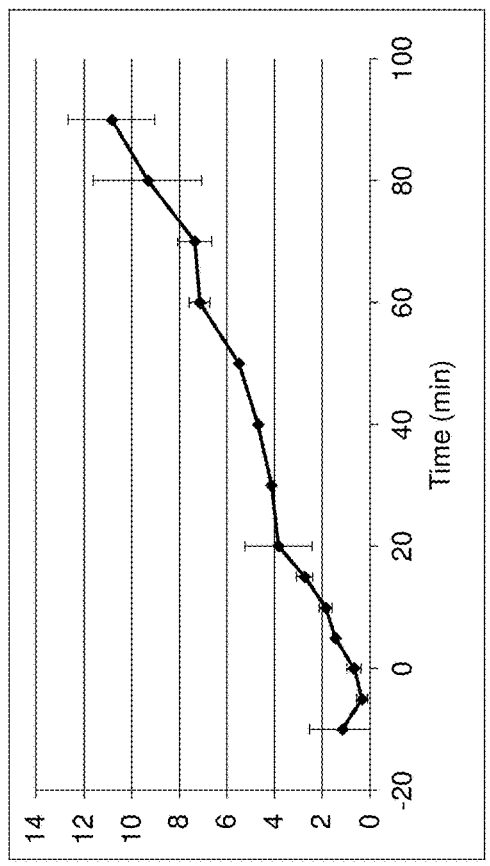
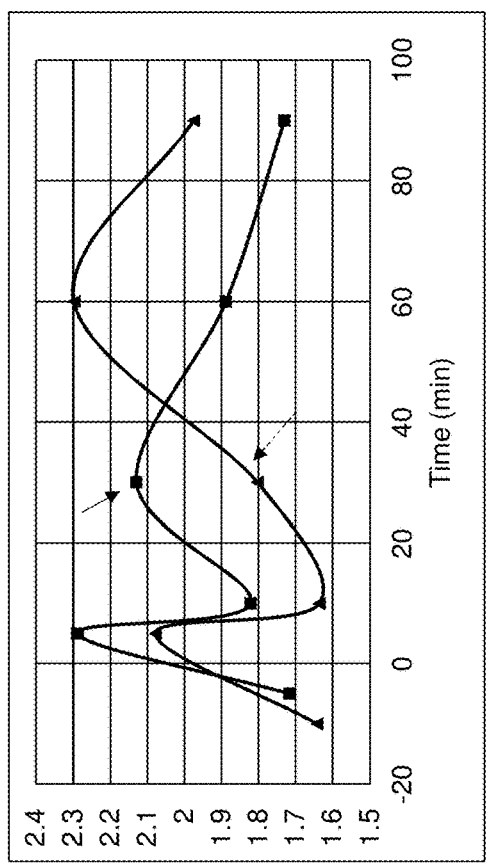
Fig. 4C
Fig. 4B

IN VITRO INTESTINAL DRUG DISPOSITION DEVICE

CROSS-REFERENCE TO RELATED APPLICATIONS

This is a U.S. national phase application under 35 U.S.C. § 371 of Patent Cooperation Treaty Application No. PCT/SE2018/050752, filed Jul. 9, 2018, which claims priority from Swedish Patent Application Serial No. 1751066-0, filed on Sep. 4, 2017, and which incorporates by reference those PCT and Swedish applications in their entireties.

TECHNICAL FIELD

The present invention generally relates to an in vitro intestinal drug disposition device, and to the use thereof in an in vitro intestinal drug disposition method.

BACKGROUND

A general problem in pharmaceutical industry is the low aqueous solubility of active agents during drug discovery and development. A common approach to combat this solubility problem has been to use lipid-based formulations (LBFs). In such a formulation approach, the LBFs circumvent the solubility limitations and promote drug solubilization when the drug is presented to the gastrointestinal tract.

The performance of such LBFs is investigated by conducting so called in vitro lipolysis studies mimicking the digestion taking place in the intestine. Such in vitro lipolysis studies typically utilize a digestion vessel containing the LBFs, digestive enzymes and simulated intestinal solution coupled to a titration set-up comprising a pH-stat apparatus and an autoburette containing NaOH [1-4]. Upon digestion of the LBFs, free fatty acids (FFAs) are released, resulting in a decrease in pH. The pH-stat apparatus detects the pH drop and adjusts the pH by adding NaOH from the autoburette. The extent of digestion of the LBFs is then estimated based on the amount of NaOH added over time.

Such prior art in vitro lipolysis studies of performance of LBFs provide generally poor in vitro-in vivo correlation (IVIVC) when related to in vivo performance of formulations.

The short-comings of in vitro lipolysis have been addressed in the prior art. For instance, in silico approaches have been used to simulate LBF digestion employing biopharmaceutical modeling [1]. Others have made use of a combination of in vitro lipolysis studies and in situ studies, in which the bioavailability of an active agent is determined from blood samples following administration of digested LBFs directly to the intestine of the test animals [2]. Another approach has been to complement the in vitro lipolysis studies with ex vivo permeation experiments using an Ussing chamber [3]. A Franz diffusion cell has been proposed to study absorption and permeation across mucous membranes [12].

However, such prior art approaches require comparatively expensive, time consuming and cumbersome in vivo experiments or the need for running separate in vitro and ex vivo experiments, which is not optimal.

Accordingly, there is a need for a set-up allowing testing of performance of LBFs and other compounds in an efficient manner that mimics the digestion and absorption taking place in the intestine.

SUMMARY

It is a general objective to provide an in vitro intestinal drug disposition device capable of mimicking the digestion and absorption taking place in the intestine.

This and other objectives are met by embodiments as disclosed herein.

The present invention relates to an in vitro intestinal drug disposition device and an in vitro intestinal drug disposition method as defined in the independent claims. Further embodiments of the present invention are defined in the dependent claims.

The in vitro intestinal drug disposition device comprises a donor chamber configured to comprise a donor solution and having a bottom end and a top end. The device also comprises a receiver chamber configured to comprise an absorption solution and an absorption membrane arranged in between and separating the donor chamber and the receiver chamber. A first main side of the absorption membrane is configured to be in contact with the donor solution and a second, opposite main side of the absorption membrane is configured to be in contact with the absorption solution. A ratio of an internal volume of the donor chamber to an area of the first main side of the absorption membrane is equal to or smaller than 3 ml/cm$^2$. A cross-sectional area of the donor chamber at the bottom end is larger than a cross-sectional area of the donor chamber at the top end.

A system for in vitro intestinal drug disposition comprises an in vitro intestinal drug disposition device according to the present invention. The in vitro intestinal drug disposition device has a receiver chamber comprising a sampling port configured to provide access to an internal volume of the receiver chamber. The donor chamber of the in vitro intestinal drug disposition device comprises a sampling port configured to provide access to the internal volume of the donor chamber. Alternatively, or in addition, the in vitro intestinal drug disposition device comprises a chamber lid for the donor chamber. The chamber lid comprises a sampling port configured to provide access to the internal volume of said donor chamber. The system also comprises an analysis device comprising an analysis probe arranged in an opening in the chamber lid or in the sampling port of the donor chamber.

The in vitro intestinal drug disposition method comprises adding a test substance to the donor chamber of an in vitro intestinal drug disposition device according to the embodiments. The donor chamber of the in vitro intestinal drug disposition device comprises a donor solution and the receiver chamber comprises an absorption solution. The method also comprises determining concentration of the test substance and/or a digestion metabolite of the test substance in at least one of the donor solution and the absorption solution at one or more time instances.

The in vitro intestinal drug disposition device mimics both the digestion and absorption processes taking place in the intestine. Accordingly, the in vitro intestinal drug disposition device has higher biorelevance as compared to prior art in vitro lipolysis devices.

BRIEF DESCRIPTION OF THE DRAWINGS

The embodiments, together with further objects and advantages thereof, may best be understood by making reference to the following description taken together with the accompanying drawings, in which:

FIG. 4B is a diagram illustrating supersaturation rate (SR) vs. time of a model compound (danazol) in the absence (squares, indicated by full arrow) and presence (triangles, indicated by hatched arrow) of an absorption membrane and a receiver chamber for test formulation type IIIB-LC.

FIG. 4C is a diagram illustrating mass transfer of a model compound (danazol) across the absorption membrane over time for test formulation type IIIB-LC. Values are expressed as average values±SD (n=3).

DETAILED DESCRIPTION

The present invention generally relates to an in vitro intestinal drug disposition device, and to the use thereof in an in vitro intestinal drug disposition method.

The in vitro intestinal drug disposition device of the present invention is based on having donor and receiver chambers separated by an absorption membrane. This design of the in vitro intestinal drug disposition device with separate chambers more correctly reflects the environment in the intestine, with the donor chamber corresponding to the intestinal volume, the absorption membrane mimicking the intestinal mucosa and the receiver chamber corresponding to the blood system with blood vessels in the walls of the intestine.

The in vitro intestinal drug disposition device can thereby be used not only to study in vitro lipolysis but also the absorption process that occurs in the intestine. Accordingly, the lipolysis or digestion and the absorption are connected and occur in the same in vitro intestinal drug disposition device during the same experiment. This is a main advantage of the present invention as compared to prior art solutions [1-4], in which the dynamics of digestion and absorption processes cannot be captured in a single experimental set-up but require separate evaluations. The present invention thereby more correctly reflects and captures the digestion and absorption taking place in the intestine, effectively contributing to a high IVIVC. Furthermore, the prior art approaches require comparatively expensive, time consuming and cumbersome in vivo experiments or the need for running separate in vitro and ex vivo experiments where the digestion and absorption are explored in parallel rather than in one assay, which is not optimal. A further advantage of having an absorption membrane and a receiver chamber in the in vitro intestinal drug disposition device of the present invention is that the absorption reduces the risk of drug precipitation that may otherwise occur in in vitro lipolysis studies due to achieving a high concentration of the drug and reaching a supersaturated state. The continuous absorption taking place over the absorption membrane and into the receiver chamber operating as a drug sink, lowers the drug concentration in the donor chamber and prevent undesired drug precipitation.

Figure 1:
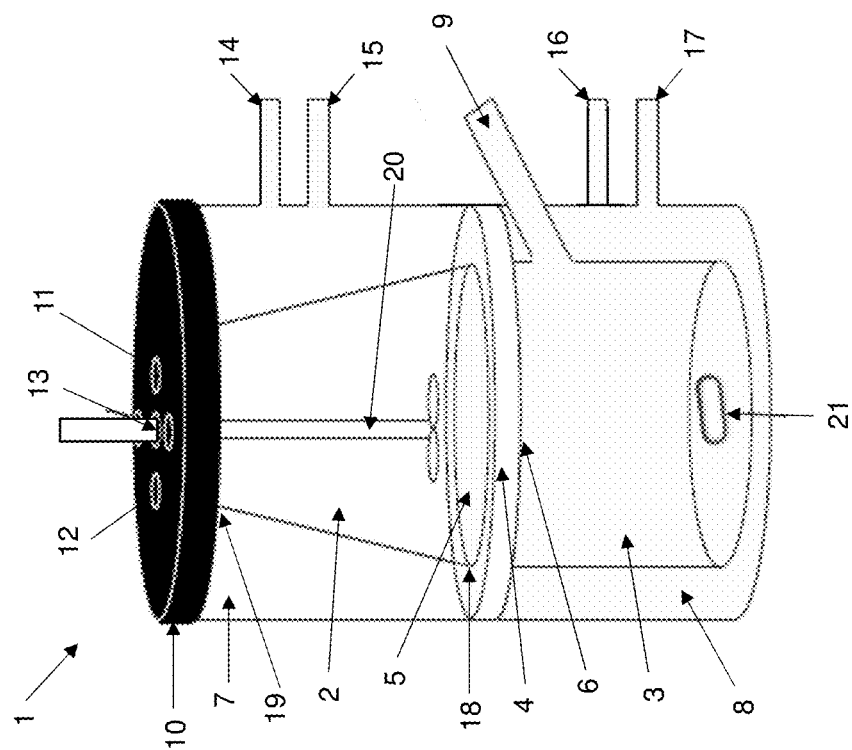
FIG. 1 is a schematic illustration of an in vitro intestinal drug disposition device according to an embodiment.

FIG. 1 is a schematic illustration of an in vitro intestinal drug disposition device 1 according to an embodiment. In an aspect of the present invention, the in vitro intestinal drug disposition device 1 comprises a donor chamber 2 configured to comprise a donor solution. The donor chamber 2 has a bottom end 18 and a top end 19. The in vitro intestinal drug disposition device 1 also comprises a receiver chamber 3 configured to comprise an absorption solution and an absorption membrane 4 arranged in between and separating the donor chamber 2 and the receiver chamber 3. According to the invention, a first main side 5 of the absorption membrane 4 is configured to be in contact with the donor solution and a second, opposite main side 6 of the absorption membrane 4 is configured to be in contact with the absorption solution.

A ratio of an internal volume of the donor chamber 2 to an area of the first main side 5 of the absorption membrane 4 is equal to or smaller than 3 ml/cm². Furthermore, a cross-sectional area of the donor chamber 2 at the bottom end 18 is larger than a cross-sectional area of the donor chamber 2 at the top end 19.

The in vitro intestinal drug disposition device 1 thereby comprises two chambers 2, 3 separated by the absorption membrane 4. The first or upper chamber is the donor chamber 2 that is configured to comprise a donor solution that mimics the intestinal environment. Accordingly, the donor solution preferably comprises constituents or ingredients that resembles the environment and chemicals present in the intestine. The donor solution is therefore preferably selected among so-called lipolysis media or simulated intestinal media used in in vitro lipolysis studies. Such a lipolysis medium is typically a buffer solution comprising simulated intestinal fluid with bile secretion components. The donor solution preferably has a pH corresponding to the pH in the relevant part of the intestine. The donor chamber 2 can also simulate the gastric-to-intestinal transfer through pH-shift and addition of concentrated lipolysis solution mimicking the intestinal fluid.

Correspondingly, the absorption solution in the receiver chamber 3 as second or lower chamber should preferably mimic the blood or blood plasma in the blood vessels in the intestine. Accordingly, the absorption solution preferably comprises constituents or ingredients that resemble the blood plasma and preferably the pH of the blood plasma.

The in vitro intestinal drug disposition device 1 has a low ratio of the internal volume of the donor chamber 2 to the area of the first main side 5 of the absorption membrane 4, and in particular of the area of a portion of the first main side 5 of the absorption membrane 4 enclosed by donor chamber 2. Thus, the area of the portion of the first main side 5 of the absorption membrane 4 enclosed by and lying within a circumference of the bottom end 18 of the donor chamber 2. This ratio is thereby equal to or smaller than 3 ml/cm². This low ratio reflects the in vivo situation in the intestine, which has a large area of the intestinal mucosa as compared to the volume in the intestine. Thus, the low ratio of the internal volume of the donor chamber 2 to the area of the first main side 5 of the absorption membrane 4 simulates the absorption conditions in the intestine and thereby contributes to the high biorelevance of the in vitro intestinal drug disposition device 1.

In an embodiment, the ratio of the internal volume of the donor chamber 2 to the area of the first main side 5 of the absorption membrane 4 is preferably equal to or smaller than 2.5 ml/cm², and in particular equal to or smaller than 2.25 ml/cm², and more preferably equal to or smaller than 2.1 or 2 ml/cm². The ratio may be even lower, such as equal to or smaller than 1.5 ml/cm² or equal to or smaller than 1 ml/cm². It is also possible to have even lower ratios, for instance, a ratio of equal to or smaller than 0.9 ml/cm², equal to or smaller than 0.8 ml/cm², equal to or smaller than 0.7 ml/cm², equal to or smaller than 0.6 ml/cm² or equal to or smaller than 0.5 ml/cm².

As mentioned in the foregoing, the donor chamber 2 is configured to comprise a volume of the donor solution. In an embodiment, a ratio of the volume of the donor solution to the area of the first main side 5 of the absorption membrane 4 is equal to or smaller than 3 ml/cm². In a preferred embodiment, the ratio of the volume of the donor solution to the area of the first main side 5 of the absorption membrane 4 is equal to or smaller than 2.5 ml/cm², and more preferably equal to or smaller than 2.25 ml/cm², such as equal to or smaller than 2.1 or 2 ml/cm². The ratio may be even lower, such as equal to or smaller than 1.5 ml/cm² or equal to or smaller than 1 ml/cm². It is also possible to have even lower ratios, for instance, a ratio of equal to or smaller than 0.9 ml/cm², equal to or smaller than 0.8 ml/cm², equal to or smaller than 0.7 ml/cm², equal to or smaller than 0.6 ml/cm² or equal to or smaller than 0.5 ml/cm².

The donor chamber 2 in the in vitro intestinal drug disposition device 1 according to the present invention has a comparatively larger area of the bottom end 18 as compared to the area of its top end 19. Thus, the cross-sectional area of the donor chamber 2 at the bottom end 18 is larger than the cross-sectional area of the donor chamber 2 at the top end 19. The cross-sectional areas at the bottom and top ends 18, 19 are preferably perpendicular to an axis running from the bottom end 18 to the top end 19 of the donor chamber 2. This axis is preferably perpendicular to the first main side 5 of the absorption membrane 4. Expressed differently, the cross-sectional areas at the bottom and top ends 18, 19 of the donor chamber 2 are preferably parallel with the absorption membrane 4, and in particular parallel with the first main side 5, and preferably also the second, opposite main side 6, of the absorption membrane 4. The larger bottom area of the donor chamber 2 as compared to the top area furthermore contributes to having a comparatively small internal volume of the donor chamber 2 but a comparatively large area of the first main side 5 of the absorption membrane 4.

In an embodiment, the cross-sectional area of the donor chamber 2 is continuously or step-by-step decreasing from the bottom end 18 towards the top end 19. Thus, when travelling from the bottom end 18 of the donor chamber 2 along the above mentioned axis towards the top end 19 of the donor chamber 2 the cross-sectional area of the donor chamber 2 preferably decreases. The decrease in cross-sectional area can be continuous as shown in FIG. 1. This case corresponds to having a cone-shaped donor chamber 2. Instead of having a continuously decreasing cross-sectional area, the cross-sectional area could decrease in one or multiple, i.e., at least two, steps. Such a case would correspond to having a donor chamber 2 in the form of multiple co-axial cylinders with ever decreasing diameter when going from a bottom cylinder at the bottom end 18 of the donor chamber 2 to a top cylinder at the top end 19 of the donor chamber 2. It is also possible to combine these two cases, i.e., to have a donor chamber 2, the cross-sectional area of which is decreasing continuously along a part of the height of the donor chamber 2 from the bottom end 18 to the top end 19, whereas another part of the height of the donor chamber 2 has a cross-sectional area that decreases in steps.

In a particular embodiment, the donor chamber 2 is a cone-shaped donor chamber 2 and the receiver chamber 3 is a cylinder-shaped receiver chamber 3. In a preferred embodiment, the diameter of the cone-shaped donor chamber 2 at its bottom end 18 is preferably equal to or smaller than, preferably equal to, the diameter of the cylinder-shaped receiver chamber 3 at its top end, i.e., the end of the cylinder-shaped receiver chamber 3 facing the second, opposite side 6 of the absorption membrane 4. The design of the donor chamber 2 in the in vitro intestinal drug disposition device 1 according to the present invention achieves several advantages to the device 1 and the uses thereof. Firstly, the decreasing diameter of the donor chamber 2 implies that the bottom area of the donor chamber 2 and thereby the first main side 5 of the absorption membrane 4 can be kept large while still having a comparatively small internal volume of the donor chamber 2, for instance as compared to having a cylinder-shaped donor chamber with a same diameter at the top end 19 as at the bottom end 18. The decreasing diameter of the donor chamber 2 additionally implies that the donor chamber height, i.e., from the bottom end 18 to the top end 19, can be sufficiently large to include an analysis probe, such as pH probe, in the donor chamber 2 to perform measurements in the donor solution. Furthermore, or in addition, a stirrer 20 could be included in the donor chamber 2. Thus, if the donor chamber 2 instead would have uniform diameter or even increasing diameter when going from the bottom end 18 to the top end 19 the height of the donor chamber 2 and thereby the maximum depth of any donor solution present in the donor chamber 2 must be kept very low in order to keep the total internal volume of the donor chamber 2 and the ratio between this internal volume and the area of the first main side 5 of the absorption membrane 4 low. The low height may then prevent insertion of an analysis probe and/or stirrer in the donor solution to have the probe head or sensor of the analysis probe or the stirring head of the stirrer fully immersed in the donor solution to perform an accurate measurement or mixing, respectively. Thirdly, the particular design of the donor chamber 2 of the present invention furthermore facilitates sampling of donor solution during operation and use of the in vitro intestinal drug disposition device 1 as will be further described herein. In addition, the sufficiently large donor chamber height further allows efficient stirring in the donor chamber 2. As is further described herein, a stirrer 20 can thereby be arranged in the donor chamber 2 to achieve an efficient stirring and mixing of the donor solution. A low height donor chamber 2 would not enable having such a stirrer 20 and would thereby suffer from poor donor solution mixing.

In an embodiment, a ratio of the internal volume of the donor chamber 2 to an internal volume of the receiver chamber 3 is smaller than 1. In other words, the internal volume of the receiver chamber 3 is preferably larger than the internal volume of the donor chamber 2. Such a design of the two chambers 2, 3 implies that the receiver chamber 3 can effectively operate as a sink chamber. Thus, there will be a driving force of absorption of a drug or its metabolite from the donor chamber 2 through the absorption membrane 4 and into the receiver chamber 3.

In the intestine, any drugs or drug metabolites that are absorbed by the intestinal mucosa and enters the blood vessels in the intestinal walls will be transported away by the blood system to other parts of the body. Accordingly, the concentration of the drug or drug metabolite will generally be lower in the blood side of the intestinal mucosa as compared to in the intestinal side. Having a comparatively larger internal volume of the receiver chamber 3 as compared to of the donor chamber 2 mimics this concentration gradient but without the need of a continuous absorption solution flow through the receiver chamber 3. This means as drugs or drug metabolites are released in the in vitro lipolysis taking place in the donor solution in the donor chamber 2 the concentration gradient will drive the absorption of the drugs or drug metabolites across the absorption membrane 4 and into the receiver chamber 3 and the receiver solution present therein. This thereby corresponds to the diffusion or transport taking place across the intestinal mucosa in the intestine.

In a preferred embodiment, the ratio of the internal volume of the donor chamber 2 to the internal volume of the receiver chamber 3 is equal to or smaller than ½ and more preferably equal to or smaller than ⅓.

In an embodiment, the donor chamber 2 is configured to comprise a volume of the donor solution and the receiver chamber 3 is configured to comprise a volume of the absorption solution. In an embodiment, the ratio of the volume of the donor solution to the volume of the absorption solution is preferably smaller than 1, more preferably equal to or smaller than ½, such as equal to or smaller than ⅓.

The receiver chamber 3 should preferably maintain sink conditions. Accordingly, its volume is preferably larger than the volume of the donor chamber 2 as mentioned in the foregoing. It is alternatively, or in addition, possible to maintain such sink conditions by designing the receiver chamber 3 as a flow through chamber. In such a case, the receiver chamber 3 comprises a flow input and a flow output (not shown). The absorption solution is then allowed to flow, such as by one or more pumps, through the flow input and into the receiver chamber 3 and then further out from the receiver chamber through the flow output.

In an embodiment, the donor chamber 2 comprises a first fluid jacket 7 configured to comprise a fluid and the receiver chamber 3 correspondingly comprises a second fluid jacket 8 configured to comprise a fluid. Thus, the two chambers 2, 3 are, in this embodiment, enclosed by a respective fluid jacket 7, 8 configured to comprise a fluid. The fluid jackets 7, 8 and the fluids present therein can thereby be used to achieve a temperature control of the donor chamber 2 and the receiver chamber 3, and in particular by the donor solution and absorption solution present therein. Thus, the fluid present in the first fluid jacket 7 has a temperature within a first temperature range and the fluid present in the second fluid jacket 8 has a temperature within a second temperature range. In an embodiment, the first and second temperature ranges are the same, i.e., the temperature of the fluids present in the two fluid jackets 7, 8 is the same or at least substantially the same, i.e., the difference in temperature of the two fluids is smaller than some defined maximum temperature difference, e.g., smaller than 1-5° C. as an illustrative, but non-limiting, example. A typical example would be to have a temperature control of the donor and receiver chambers 2, 3 and of the donor and absorption solutions to be at or at least close to 37° C. corresponding to the normal body temperature of a human being. If the in vitro intestinal disposition device 1 is used to analyze drug solubility and/or LBF performance in other, non-human animals, and in particular other non-human mammals, the temperature of the fluids in the two fluid jackets 7, 8 is preferably set according to the body temperature of that particular animal.

In another embodiment, the first and second temperature ranges may be different, i.e., the temperature of the fluid in the first fluid jacket 7 may be different from the temperature of the fluid in the second fluid jacket 8. As an example, for drug disposition studies over nasal mucosa or skin, the donor chamber 2 could be kept at 32° C. whereas the receiver chamber 3 could be kept at 37° C.

The first fluid jacket 7 preferably has a fluid input 14 and a fluid output 15 to enable a flow of the tempered fluid into and out from the first fluid jacket 7. This continuous flow of fluid through the first fluid jacket 7 enables an efficient temperature control to achieve a stable, non-varying temperature within the donor chamber 2. Correspondingly, the second fluid jacket 8 preferably has a fluid input 16 and a fluid output 17 to enable a corresponding flow of the tempered fluid into and out from the second fluid jacket 8.

The fluid inputs 14, 16 and fluid outputs 15, 17 are preferably arranged in the walls of the first and second fluid jackets 7, 8 as indicated in FIG. 1. The fluid inputs 14, 16 are then preferably connectable to a same or different fluid sources and the fluid outputs 15, 17 are preferably connectable to a same or different fluid sinks. As an example, the fluid inputs 14, 16 and fluid outputs 15, 17 can be connected to a temperature-controlled water bath. In addition, one or more fluid pumps may be connected to the fluid inputs 14, 16 and/or fluid outputs 15, 17 to achieve a flow of the fluids through the fluid jackets 7, 8.

Any fluid, preferably liquid or gas, and more preferably liquid, that can be used to achieve a temperature control in the in vitro intestinal drug disposition device 1 can be employed according to the embodiments. A currently preferred example of such a fluid is water but any fluid could be used depending on the particular desired temperature interval. The same type of fluid could be used in both fluid jackets 7, 8 or different types of fluids could be used in the two fluid jackets 7, 8.

A further advantage of having a donor chamber 2 with decreasing diameter when going from the bottom end 18 to the top end 19 is obtained when having the first fluid jacket 7. The particular shape of the donor chamber 2 then allows for a larger volume of circulating fluid in the first fluid jacket 7 and thereby a more efficient maintenance of the temperature of the donor chamber 2 and the donor solution present therein.

The absorption membrane 4 of the in vitro intestinal drug disposition device 1 should preferably mimic the absorption taking place across the intestinal mucosa. In a particular embodiment, the absorption membrane 4 is a semipermeable membrane comprising a cell layer on the first main side 5 of the absorption membrane 4. In such an embodiment, the cell layer corresponds to the cell lining of the intestinal mucosa. The cell type used in the cell layer depends on the particular experiment. An example of cells that could be used is epithelial colonic cells, such as represented by the Caco-2 cells. The embodiments are, however, not limited thereto but can rather use other cell lines and types, including other epithelial cell lines commonly used for intestinal studies, such as Madin Darby Canine Kidney (MDCK) epithelial cells. In either case, the cell layer is provided on the main side of the absorption membrane 4 facing the donor chamber 2 and thereby being, when in use, in contact with the donor solution, i.e., the first main side 5 of the absorption membrane 4. The cell layer could be in the form of a monolayer, i.e., the cell layer is on average one cell thick, or in the form of a multi cell layer, i.e., consisting of more than one layer of cells. All of the cells in the cell layer may be of the same cell line, strain or type. It is, however, possible to cells of different cell lines, strains or types in the cell layer if desired. For instance, microbes could be added to mimic the microbiota present in the intestine. Caco-2 cells represent enterocytes. Other intestinal epithelial cells could also, or alternatively, be added, such as mucus-producing cells, such as cell line HT29. Alternatively, or in addition, immune cells, such as monocytes, could be added.

In other embodiments, the absorption membrane 4 is not necessary a semipermeable membrane comprising a cell layer. In clear contrast, a semipermeable membrane without any cells could be used as an artificial membrane mimicking the intestinal mucosa. For instance, artificial membranes with a hydrophobic layer may be used as absorption membrane 4, such as hexadecane membrane, phospholipid membrane or hydrophobic cellulose.

In an embodiment, the donor chamber 2 comprises a sampling port configured to provide access to the internal volume of the donor chamber 2 and the receiver chamber 3 comprises a sampling port 9 configured to provide access to an internal volume of the receiver chamber 3. Such sampling ports 9 may then be arranged in the wall of the donor chamber 2 and the receiver chamber 3 as illustrated in FIG. 1 for the receiver chamber 3.

In another embodiment, the in vitro intestinal drug disposition device 1 comprises a chamber lid 10 for the donor chamber 2. The chamber lid 10 then comprises a sampling port 11 configured to provide access to the internal volume of the donor chamber 2. In this embodiment, the receiver chamber 3 comprises a sampling port 9 configured to provide access to an internal volume of the receiver chamber 3. The sampling port 11 in the chamber lid 10 may be in the form of a through-hole in the chamber lid 10 to allow taking samples of the donor solution present in the donor chamber 2. Correspondingly, the sampling port 9 for the receiver chamber 3 could be in the form of a port or tube running from a wall in the receiver chamber 3 and through the optional but preferred second fluid jacket 8 as shown in FIG. 1. This sampling port 9 thereby enables taking samples of the absorption solution present in receiver chamber 3.

In an embodiment, the donor chamber 2 comprise a first sampling port and the chamber lid 10 may then comprise a second sampling port 11. Thus, in this embodiment, the in vitro intestinal drug disposition device 1 comprises at least two sampling ports configured to provide access to the internal volume of the donor chamber 2.

Alternatively, or in addition, analysis equipment, such as an analysis probe, could be inserted into the donor and/or absorption solution via the respective sampling port 9, 11.

Another aspect of the present invention relates to a system for in vitro intestinal drug disposition. This system comprises an in vitro intestinal drug disposition device 1 according to the present invention. The in vitro intestinal drug disposition device 1 has a receiver chamber 3 comprising a sampling port 9 configured to provide access to an internal volume of the receiver chamber 3. The donor chamber 2 of the in vitro intestinal drug disposition device 1 comprises a sampling port configured to provide access to the internal volume of the donor chamber 2. Alternatively, or in addition, the in vitro intestinal drug disposition device 1 comprises a chamber lid 10 for the donor chamber 2. The chamber lid 10 comprises a sampling port 11 configured to provide access to the internal volume of said donor chamber 2. The system also comprises an analysis device comprising an analysis probe arranged in an opening 12 in the chamber lid 10 or in the sampling port of the donor chamber 2.

As mentioned in the foregoing, the preferred design of the donor chamber 2 allows immersion of at least a head of the analysis probe into the donor solution present in the donor chamber 2 to perform various measurements. In a particular embodiment, the analysis device is a pH meter configured to measure a pH of the donor solution. In a preferred embodiment, the system also comprises a dispensing device configured to dispense a pH adjusting agent into the donor solution in response to a pH change of the donor solution measured by the pH meter. An example of such a dispensing device is an autoburette comprising a base, such as NaOH, that is added to the donor solution in response to any detected pH change, e.g., pH reduction, of the donor solution as measured by the pH meter. Thus, in the case of LBF lipolysis, FFAs are released into the donor solution upon digestion of the LBFs, resulting in a decrease in pH. A pH meter, such as part of a pH-stat apparatus, detects the pH drop and adjusts the pH by adding, for instance, NaOH from an autoburette as illustrative example of a dispensing device. The rate and extent of digestion of the LBFs can be estimated and monitored based on the amount of NaOH added over time.

A pH meter should merely be seen as an illustrative, but non-limiting, example of analysis device of the system. Other analysis devices could be used instead or, or as a complement of the pH meter. In the latter case, the chamber lid 10 preferably comprises different openings 12 for different analysis probes as schematically illustrated in FIG. 1. Examples of such other analysis devices include Raman and UV probes, etc. to analyze, detect or measure molecules, solid form of precipitates, rate of formation of e.g., digestion products and, hence, digestion kinetics and rate of formation of solids and, hence, precipitation kinetics present in the donor solution and/or in the absorption solution.

In an embodiment, the system also comprises a magnetic stir bar 21 provided in the receiver chamber 3 and a stirrer 20 provided in the donor chamber 2 and having a shaft arranged in an opening 13 of the chamber lid 10. The magnetic stir bar 21 enables an efficient and continuous mixing of the absorption solution during use of the in vitro intestinal drug disposition device 1. The stirrer 20 correspondingly enables an efficient and continuous mixing of the donor solution during use. The magnetic stir bar 21 and the stirrer 20 are furthermore arranged in such a way that solution sampling through the sampling ports 9, 11 and measurements by an analysis probe can performed even though mixing is taking place in the donor chamber 2 and in the receiver chamber 3. The improved mixing or stirring is an advantage of the in vitro intestinal drug disposition device 1, reflecting the in vivo environment, increasing the reliability of measurements performed by the analysis device(s).

An example of setting up the in vitro intestinal drug disposition device 1 is described here below. Tubing from a water bath are attached to the input and output ports 14, 15, 16, 17 of the fluid jackets 7, 8 to fill the fluid jackets 7, 8 with warm circulating water. The absorption solution to be used in the receiver chamber 3 is prepared and filled into the receiver chamber 3. A magnetic stir bar 21 is added to the receiver chamber 3 in order to enable mixing of the absorption solution. Optionally, rubber rings (not illustrated) are put in designated grooves to avoid leakage between the donor chamber 2 and the receiver chamber 3. An absorption membrane 4 of choice is placed between the two chambers 2, 3 and the chambers 2, 3 are mounted together. Donor solution is added to the donor chamber 2. The in vitro intestinal drug disposition device 1 is closed with the chamber lid 10 and required equipment, such as stirrer 20, pH probe, autoburette, etc., is inserted into the donor solution and/or the absorption solution. The experiment can then be started by adding the formulation to be assessed through the sampling port 11 in the chamber lid 10. Digestion enzymes may also be added. Required parameters can be continuously monitored using the analysis probe(s). At any desired point in time samples can be taken from the donor chamber 2 and the receiver chamber 3.

Figure 2:
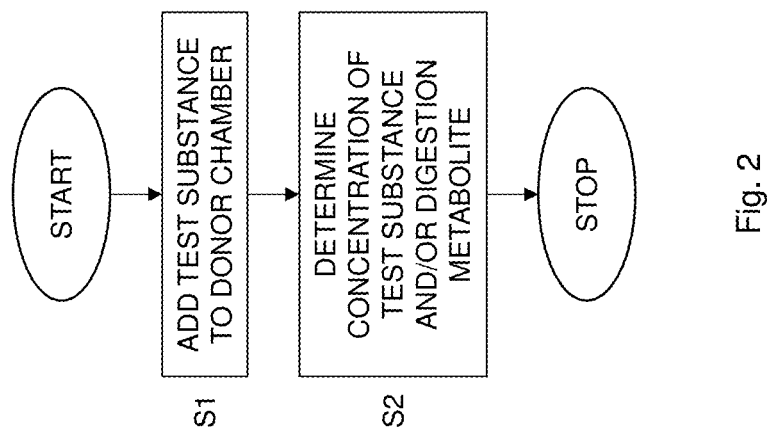
FIG. 2 is a flow chart of an in vitro intestinal drug disposition method according to an embodiment.

FIG. 2 is a flow chart of an in vitro intestinal drug disposition method according to the present invention. The method comprises adding a test substance to the donor chamber 2 of an in vitro intestinal disposition device 1 according to any of the embodiments in step S1. The donor chamber 2 comprises a donor solution, such as a donor solution mimicking an intestinal environment, e.g., a simulated intestinal fluid or solution, and the receiver chamber 3 comprises an absorption solution, such as an absorption solution mimicking blood or blood plasma. A next step S2 comprises determining concentration of the test substance and/or a digestion metabolite of the test substance in at least one of the donor solution and the absorption at, at least, one time instance.

The digestion metabolite could be any metabolite or digestion product obtained following digestion of the test substance in the donor solution. Examples of such digestion metabolites in the case of drug-loaded LBFs include the drug and FFAs.

In an embodiment, step S2 comprises determining the concentration of the test substance and/or the digestion metabolite of the test substance in at least one of the donor solution and the absorption solution at multiple time instances.

In a particular embodiment, the method also comprises determining a mass transfer of the test substance and/or the digestion metabolite of the test substance over the absorption membrane 4 based on the concentrations of the test substance and/or the digestion metabolite of the test substance determined at the multiple time instances. Thus, by measuring the concentration of the test substance and/or of the digestion metabolite in the donor solution and/or absorption solution at multiple time instances it is possible to determine a mass transfer of the test substance and/or of the digestion metabolite over the absorption membrane 4. Such mass transfer is representative of the absorption of the test substance or its digestion metabolite taking place in the intestine in vivo.

In an embodiment, step S2 comprises determining the concentration of the test substance and/or the digestion metabolite of the test substance in the donor solution and in the absorption solution at multiple time instances.

In a particular embodiment, the method also comprises determining distribution of the test substance and/or the digestion metabolite of the test substance in the donor solution and in the absorption solution based on the concentrations of the test substance and/or the digestion metabolite of the test substance determined at the multiple time instances. Thus, it is possible to determine and monitor the digestions of the test substance in the donor solution as seen as a decrease in concentration of the test substance in the donor solution and an increase in the digestion metabolite in the donor solution. In most experimental set-ups, the test substance is not digested but rather the lipids in the LBFs. The test substance can, though, be metabolized by added digestion enzymes, such as such enzymes present in cells of the absorption membrane. Hence, digestion metabolites as used herein could be digestion metabolites of lipids, digestion metabolites of the test substance or digestion metabolites of the lipids and of the test substance. It is possible to monitor the absorption of the test substance and/or digestion metabolite over the absorption membrane 4 by measuring the concentration of the test substance and/or digestion metabolite in the absorption solution.

In a particular embodiment, the method comprises measuring a pH of the donor solution and dispending a pH adjusting agent into the donor solution in response to a pH change of the donor solution.

The in vitro intestinal drug disposition device 1 is useful in evaluating the performance of drug loaded LBFs as described above. However, the in vitro intestinal drug disposition device 1 can also be used to evaluate dissolution and absorption of other formulations. These may be pharmaceutical products, food and nutraceuticals. For instance, Solid dispersions: molecular dispersion of a drug in crystalline/amorphous carrier
Soluble cyclodextrin complexes
Nanocrystals
Ordered mesoporous material Dissolution and absorption can be evaluated simultaneously. Instead of a pH meter and an autoburette, a Raman probe could be used to allow the characterization of precipitate and the solid form thereof. Alternatively, an in situ UV probe could be used to determine dissolved concentrations in real time.

Figure 7:
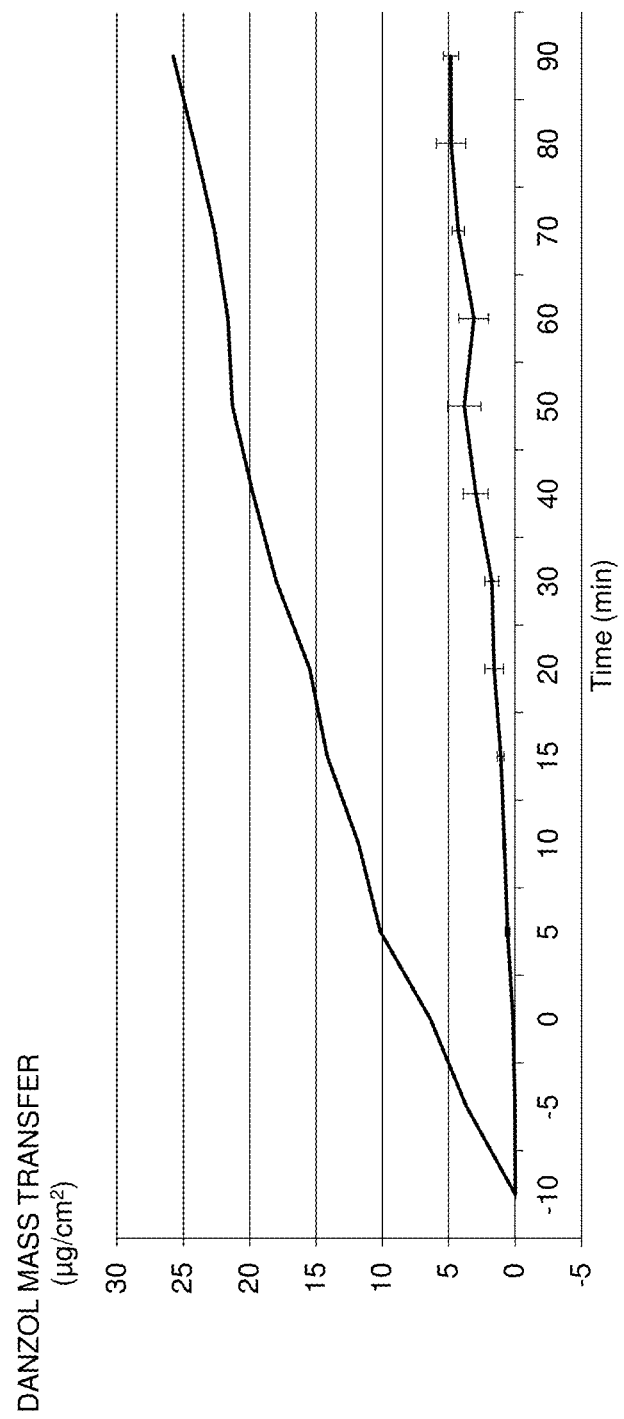
FIG. 7 is a diagram comparing absorption efficiency of unprocessed crystalline danazol (light grey) and micronized danazol (dark grey).

FIG. 7 shows an example of alternative formulations that can be evaluated using in vitro intestinal drug disposition device 1. Unprocessed crystalline danazol (light grey) shows much lower absorption as compared micronized danazol, which was ball-milled (dark grey).

The device, system and method of the present invention have mainly been described in connection with in vitro intestinal drug disposition and usage to mimic the digestion and absorption taking place in the intestine. The embodiments are, however, not limited thereto. The present invention can also be used to mimic such processes taking place over other "membranes" in a human or animal body, such as skin, or a mucosa membrane, such as bronchial mucosa, endometrium, esophageal mucosa, gastric mucosa, intestinal mucosa, nasal mucosa, olfactory mucosa, oral mucosa, penile mucosa, vaginal mucosa, frenulum of tongue, etc.

EXPERIMENTS

Experiment 1

Caco-2 cells cultured on polycarbonate filters (0.45 µm pore size, 75 mm diameter) were used as absorptive membranes in the in vitro intestinal drug disposition device of the embodiments. This is a heterogeneous human epithelial colorectal cell line derived from a colon adenocarcinoma and resembles the enterocytes lining the small intestine. After a three week period of culturing, the absorption membranes were cut out from the transwell and mounted between the two half chambers of the in vitro intestinal drug disposition device. The diameter of the opening between the two chambers was 6 cm resulting in an absorption surface of 28.27 cm$^2$.

The cone shape of the donor chamber allowed sufficiently high levels of donor solution to accurately monitor the rate and extent of digestion using a pH probe coupled to a pH stat system. Titration with an autoburette with NaOH allowed the determination of the rate and extent of digestion.

In the following examples, 60 ml of lipolysis medium was used as donor solution and contained 2 mM Tris-maleate, 1.4 mM CaCl$_2$.2H$_2$O and 150 mM NaCl supplemented with 2.24 mg/ml Fasted-State Simulated Intestinal Fluid (FaSSIF) powder at pH 6.5. This donor solution in the donor chamber mimicked the intestinal environment. The receiver chamber contained 180 ml Hank's Balanced Salt Solution (HBSS) supplemented with 4% bovine serum albumin (BSA) at pH 7.4 as absorption solution to mimic the blood.

The in vitro intestinal drug disposition device and conditions used in the following examples resulted in a ratio of the volume of the donor solution to area of absorption membrane of 2.1 ml/cm$^2$ and a ratio of the volume of the donor solution to the volume of the absorption solution mimicking blood of ⅓.

Three drug-loaded LBFs representing different groups of the Lipid Formulations Classification System (LFCS) were used in the experiment. The first LBF was of type II-LC and consisted of lipids, i.e., 32.5% (w/w) of soy bean oil (SBO) and 32.5% (w/w) Maisine 35-1, and a surfactant, i.e., 35% (w/w) TWEEN® 85. The second LBF was of type IIIB-LC and consisted of lipid, i.e., 5% (w/w) SBO, surfactant, i.e., 45% (w/w) TWEEN® 85, and co-solvent, i.e., 50% (w/w) carbitol. The third LBF was of type IV and only contained co-solvent, i.e., 50% (w/w) carbitol, and surfactant, i.e., 50% (w/w) cremophor EL. The three LBFs were loaded with the poorly soluble drug danazol, which has been used extensively to study LBFs. All LBFs were loaded with the same amount of drug (11.56 mg danazol/g LBF), which corresponded to 80% of the loading capacity of the type II-LC LBF.

Drug-loaded LBFs (1.5 g) were dispersed in the donor solution for 10 min (time −10 min until time 0 min) before digestion was initiated (at time 0 min) by adding recombinant lipase immobilized on polymer beads (Novozyme 435®; 750 mg (type II-LC and IIIB-LC) or 50 mg (type IV)). The lipid digestion resulted in the liberation of FFAs, which caused a drop in pH. The pH drop was compensated for by equimolar addition of NaOH by the autoburette. The digestion experiments were run for 90 min unless prematurely terminated due to membrane damages, as indicated below. Samples were taken from both chambers to (i) determine drug distribution in the different phases present in the intestine and (ii) determine mass transfer of the drug across the absorption membrane.

A standard experiment is performed for 90 minutes. Any damages to the membrane will result in an increase of the pH in the donor chamber due to mixing of the donor solution and the absorption solution. Such a pH increase is used as an in situ marker of damaged absorption membrane and indicates at which time point the experiment has to be terminated.

Digestion of the drug-loaded LBFs was performed in the in vitro intestinal drug disposition device and compared with digestion performed with the standard protocol in a single-chamber digestion vessel that did not include an absorption membrane separating a donor chamber and a receiver chamber, see [1-4].

The same amount of drug-loaded LBFs was added to the single chamber in the control experiments as in the donor chamber of the in vitro intestinal drug disposition device.

During digestion of the drug-loaded LBFs, the concentration of the drug in the donor solution can be higher than the apparent solubility of the drug. This means that the system is supersaturated. The rate of supersaturation (SR) can be calculated according to Equation 1:

$$\text{Supersaturation ratio} = (\text{Solubilized drug concentration})/(\text{Apparent drug solubility}) \quad (1)$$

A supersaturated system is unstable and precipitation will therefore occur. This is undesired since the solubilized drug concentration is then decreased and the driving force for absorption reduced.

In the presence of an absorption membrane and a receiver chamber, absorption of the drug provides an alternative route to drug precipitation during the supersaturated state, thereby resulting in lower drug concentrations in the donor solution, lower supersaturation and an appearance of the drug in the receiver chamber.

The following experiments were performed:
Blank LBFs, i.e., without any drug, were digested and apparent solubility of danazol was determined at different time points.
Danazol-loaded LBFs were digested in a prior art vessel [1-4] without the presence of an absorption membrane and a receiver chamber. The aqueous concentration of danazol was determined at different time points to calculate the SR.

Danazol-loaded LBFs were digested in the in vitro intestinal drug disposition device according to the embodiments. The aqueous concentration of danazol, i.e., in the donor solution, was determined at different time points to calculate the SR. In addition the appearance of danazol in the receiver was determined.

Figure 3A:
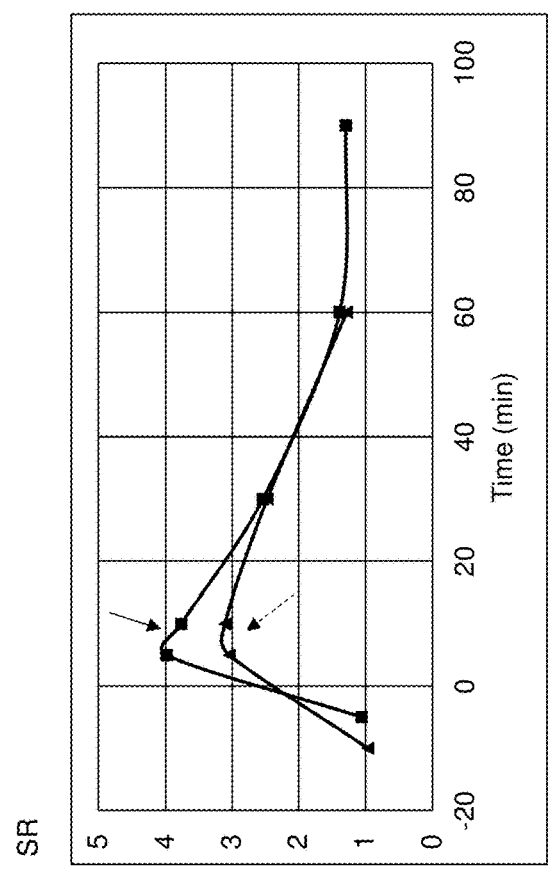
FIG. 3A is a diagram illustrating aqueous concentration vs. time profile of a model compound (danazol) in the absence (squares, indicated by full arrow) and presence (triangles, indicated by hatched arrow) of an absorption membrane and a receiver chamber for test formulation type II long chain (II-LC). Values are expressed as average values±standard deviation (SD) (n=3).
Figure 3B:
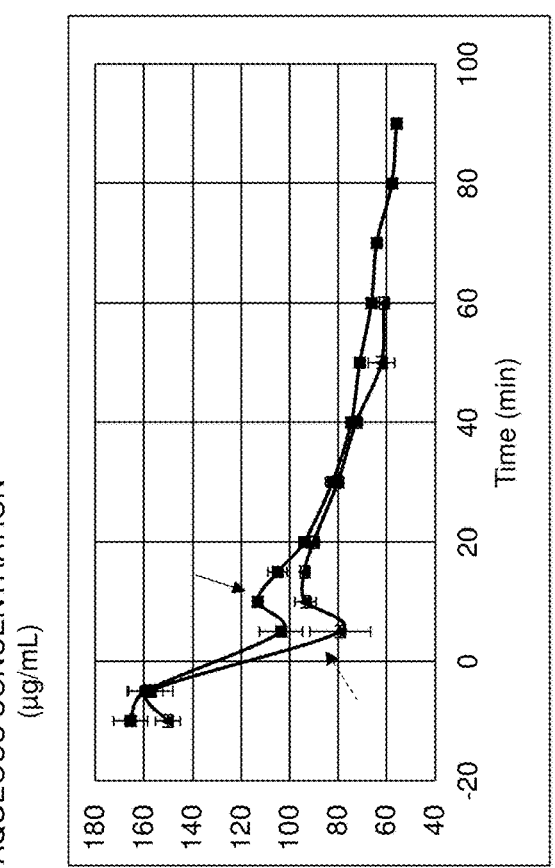
FIG. 3B is a diagram illustrating supersaturation rate (SR) vs. time of a model compound (danazol) in the absence (squares, indicated by full arrow) and presence (triangles, indicated by hatched arrow) of an absorption membrane and a receiver chamber for test formulation type II-LC.
Figures 3C, 4A:
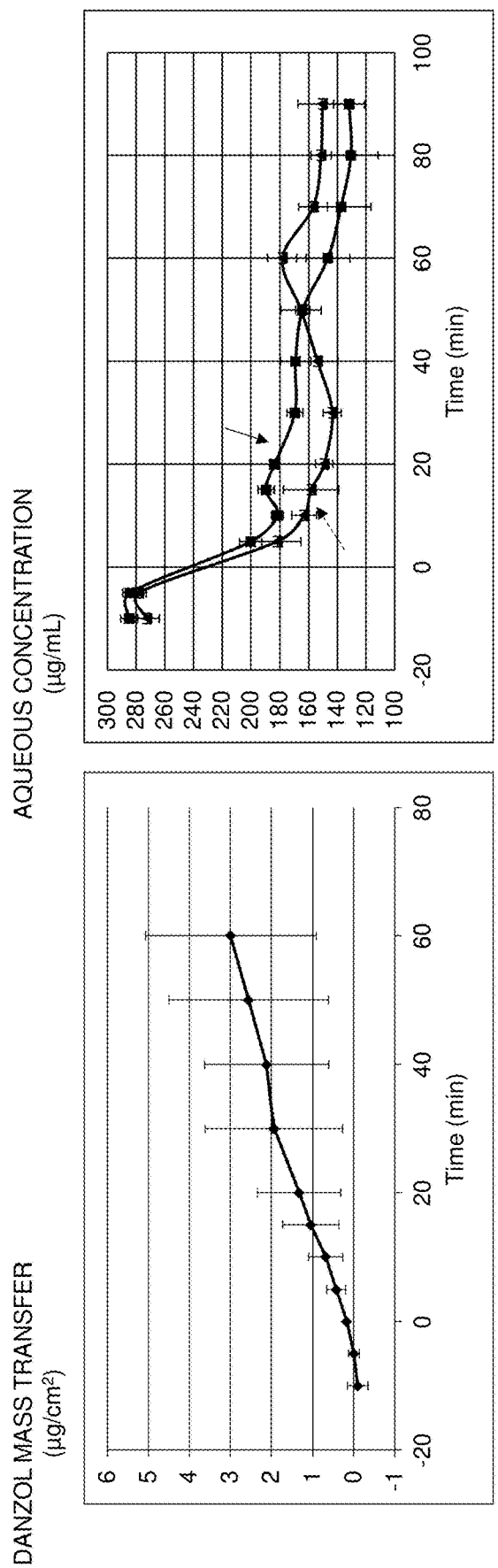
FIG. 3C is a diagram illustrating mass transfer of a model compound (danazol) across the absorption membrane over time for test formulation type II-C. Values are expressed as average values±SD (n=3).
FIG. 4A is a diagram illustrating aqueous concentration vs. time profile of a model compound (danazol) in the absence (squares, indicated by full arrow) and presence (triangles, indicated by hatched arrow) of an absorption membrane and a receiver chamber for test formulation type IIIB-LC. Values are expressed as average values±SD (n=3).
Figure 5A:
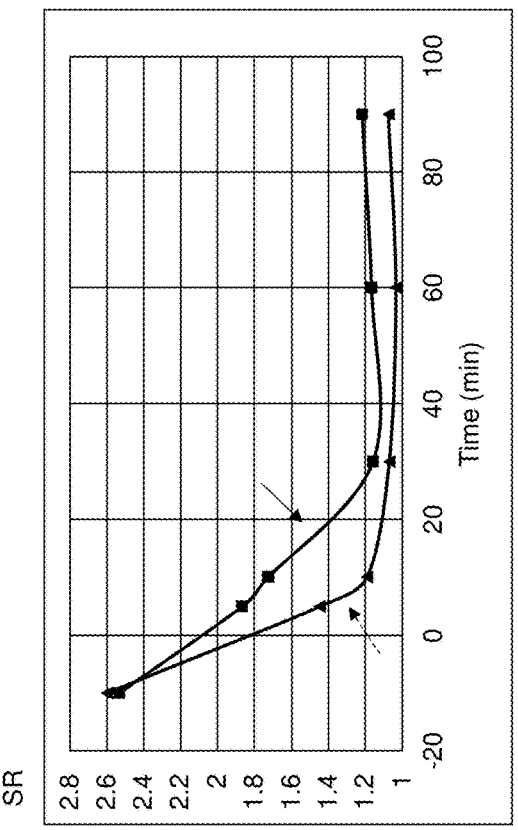
FIG. 5A is a diagram illustrating aqueous concentration vs. time profile of a model compound (danazol) in the absence (squares, indicated by full arrow) and presence (triangles, indicated by hatched arrow) of an absorption membrane and a receiver chamber for test formulation type IV. Values are expressed as average values±SD (n=3).
Figure 5B:
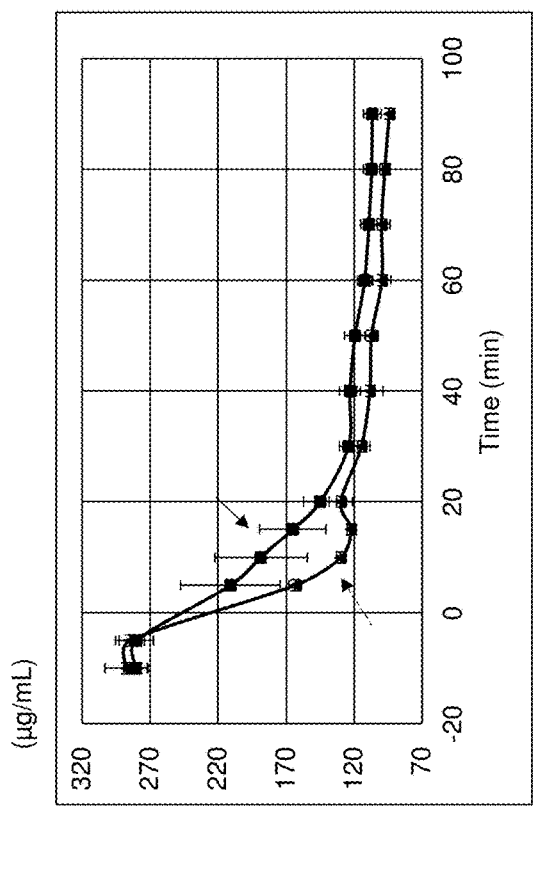
FIG. 5B is a diagram illustrating supersaturation rate (SR) vs. time of a model compound (danazol) in the absence (squares, indicated by full arrow) and presence (triangles, indicated by hatched arrow) of an absorption membrane and a receiver chamber for test formulation type IV.
Figure 5C:
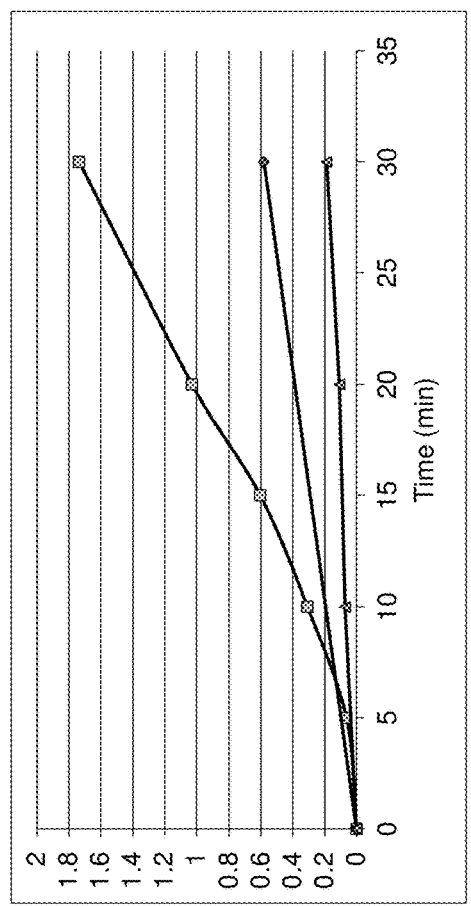
FIG. 5C is a diagram illustrating mass transfer of a model compound (danazol) across the absorption membrane over time for test formulation type IV. Values are expressed as average values±SD (n=3).

FIGS. 3A-5C illustrate the results of the experiments. In these figures, FIGS. 3A, 4A and 5A illustrate the concentration of danazol in the donor solution (aqueous concentration) vs. time in the absence (squares) and presence (triangles) of an absorption membrane and a receiver chamber. FIGS. 3B, 4B and 4B illustrate the supersaturation rate (SR) vs. time in the absence (squares) and presence (triangles) of an absorption membrane and a receiver chamber. Finally, FIGS. 3C, 4C and 5C illustrate the mass transfer of danazol across the absorption membrane over time in the in vitro intestinal drug disposition device according to the embodiments.

The in vitro intestinal drug disposition device according to the embodiments resulted in a lower aqueous concentration and SR of danazol as compared to the prior art vessel. For the IIIB-LC formulation, a higher SR was observed after 60-90 min of digestion in the in vitro intestinal drug disposition device according to the embodiments. This might result from a change in solvation capacity, i.e., the capacity of the system to keep danazol solubilized. Apart from danazol, digestion products, such as FFAs or bile salts, can be absorbed, which can change the solvation capacity.

The lower supersaturation levels obtained according to the embodiments as compared to the prior art indicated that danazol resides in a different phase than the aqueous phase of the donor solution. Indeed, FIGS. 3A-5C also show that, in addition to the digestion, absorption to the receiver chamber can be monitored. Therefore, the in vitro intestinal drug disposition device according to the embodiments captures all dynamic processes happening in the intestine after the administration of LBFs.

Experiment 2

The present experiment compared the mass transfer efficiency of an in vitro intestinal drug disposition device according to the embodiments with Transwell plates and p Flux.

Methods

Micronized danazol suspended in lipolysis buffer (pH 6.5) supplemented with 2.24 mg/ml Fasted-State Simulated Intestinal Fluid (FaSSIF) powder was used in the donor compartment of all three set-ups. The buffer was spiked with 10 μM lucifer yellow, which was used as a paracellular marker to check monolayer integrity. HBSS containing 4% bovine albumin serum was used in the receiver compartment to ensure sink conditions. Samples were taken from the receiver side to determine danazol concentrations with mass spectrometry and the fluorescence signal of lucifer yellow with a plate reader.

In Vitro Intestinal Drug Disposition Device

Caco-2 cells were grown on Transwell inserts (diameter 75 mm) and mounted in the device resulting in a surface area of 28.27 $cm^2$. The receiver compartment contained 180 ml and the donor 60 ml. A magnetic stirrer was used to mix the buffer in the receiver compartment and a stirrer propeller to mix the buffer in the donor compartment.

Transwell Plate

Caco-2 cells were grown on inserts in 12-well Transwell plates (surface area 1.12 $cm^2$). Transwell plates are typically used for in vitro absorption studies. The experiment was performed at 37° C. at 500 rpm with 400 μl of buffer at the donor and 1.2 ml of buffer at the receiver side.

μFlux

μFlux is developed by Pion Inc. to combine dissolution testing with permeation studies using μDISS profiler. Donor and receiver compartments were kept at 37° C. and typically contained 15 ml of buffer. Caco-2 cells were grown in Transwell plates and placed between the compartments resulting in a surface of 0.78 $cm^2$. Magnetic stirring was used for mixing in both the donor and receiver compartment. The μDISS profiler allowed in situ concentration monitoring with fiber optic probes. As part of the danazol binds to the BSA in the receiver compartment the optic probes could not be used to determine total concentrations in the receiver compartment. Therefore, danazol concentrations were determined with mass spectrometry.

Results

Apparent permeability (Papp) values provide information about the membrane integrity. Included experiments all resulted in a linear fraction absorbed vs. time curve for lucifer yellow indicating a constant flux across the membranes and the presence of cells. The Papp values are shown in Table 1.

TABLE 1

| Lucifer yellow Papp for the three tested devices | |
|---|---|
| | Papp ($\times 10^{-6}$ cm/s) |
| In vitro intestinal drug disposition device | 2.19 |
| Transwell plate | 1.00 |
| μFlux | 39.37 |

Figure 6:
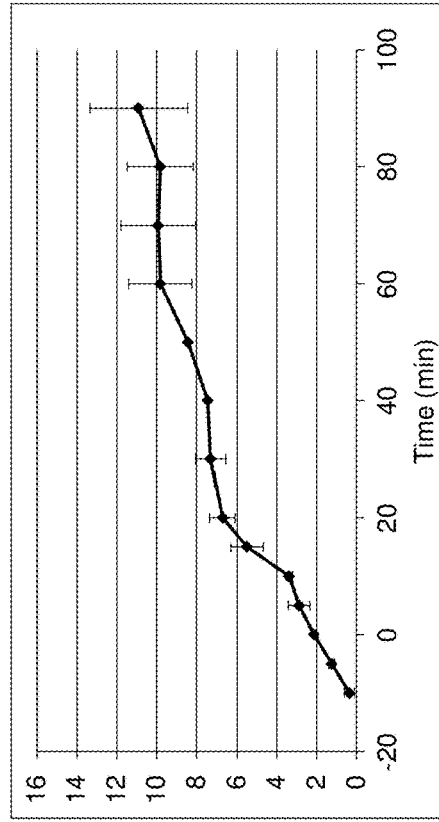
FIG. 6 is a diagram illustrating the transfer of a model compound (danazol) corrected for lucifer yellow Papp-values. The squares, diamonds and triangles represent danazol transfer for the in vitro intestinal drug disposition device, the Transwell plates and the pFlux, respectively.

The high Papp for the μFlux experiment indicated significant leakage when this membrane was used in the μFLUX. To allow direct comparison of transcellular transport of danazol in the three different set ups, the danazol transfer was corrected for lucifer yellow Papp values, see FIG. 6.

The mass transfer was highest for the in vitro intestinal drug disposition device. The relatively high flux in the in vitro intestinal drug disposition device compared to pFlux is expected to result from (i) a lower ratio of volume of donor chamber to area of absorption membrane, (ii) a lower ratio of volume of donor chamber to volume of receiver chamber and (iii) an improved stirring and, hence, reduced thickness of the unstirred water layer adjacent to the cells. Another finding was that the cells when mounted in the μFlux had reduced membrane integrity as shown through higher Papp values for lucifer yellow in the μFlux than the in vitro intestinal drug disposition device. The difference between the in vitro intestinal drug disposition device and the Transwell plates is expected to result from, among others, the difference in homogenization of the suspension. Transwell plates were placed on a shaking plate to prevent sedimentation, whereas a stirrer propeller was used the in vitro drug disposition device. Micronized danazol can have deposited on the absorption membrane, preventing permeation in the Transwell plates. The Transwell plates are typically used to study intestinal absorption for compounds in solution and are not designed to perform dissolution-permeation studies.

Experiment 3

It has previously been shown that in vitro digestion of three fenofibrate-loaded lipid-based formulations in the standard lipolysis vessel could not predict in vivo plasma exposure of fenofibrate in landrace pigs. Plasma concentration vs. time profiles, obtained after oral administration of the three formulations, were similar whereas fenofibrate exposure in the aqueous phase predicted a significant lower exposure to fenofibrate with a type IV formulation (FIG. 8A, open symbols) [5, 6].

Digestion experiments with these formulations were repeated in the in vitro intestinal drug disposition device to evaluate the capacity of the device to predict in vivo exposure of fenofibrate.

Methods

Caco-2 cells cultured on polycarbonate filters (0.45 µm pore size, 75 mm diameter) were used as absorptive membranes in the in vitro intestinal drug disposition device of the embodiments. After a three week period of culturing, the absorption membranes were cut out from the Transwell and mounted between the two chambers of the in vitro intestinal drug disposition device. The diameter of the opening between the two chambers was 6 cm resulting in an absorption surface of 28.27 $cm^2$.

The cone shape of the donor chamber allowed sufficiently high levels of donor solution to accurately monitor the rate and extent of digestion using a pH probe couple to a pH stat system. Titration with an autoburette with NaOH allowed the determination of the rate and extent of digestion.

In the following examples, 60 ml of lipolysis medium was used as donor solution and contained 2 mM Tris-maleate, 1.4 mM $CaCl_2.2H_2O$ and 150 mM NaCl supplemented with 2.24 mg/ml Fasted-State Simulated Intestinal Fluid (FaSSIF) powder at pH 6.5. This donor solution in the donor chamber mimicked the intestinal environment. The receiver chamber contained 180 ml Hank's Balanced Salt Solution (HBSS) supplemented with 4% bovine serum albumin (BSA) at pH 7.4 as absorption solution to mimic the blood.

The in vitro intestinal drug disposition device and conditions used in the following examples resulted in a ratio of the volume of the donor solution to area of absorption membrane of 2.1 ml/$cm^2$ and a ratio of the volume of the donor solution to the volume of the absorption solution mimicking blood of ⅓.

Three drug-loaded LBFs were used in the experiment. The first LBF was of type IIIA-MC and consisted of lipids, i.e., 40% (w/v) Miglyol and surfactants, i.e., 20% (w/v) Cremophor RH and 40% (w/v) TWEEN® 85. The second LBF was of type IIIA-LC and consisted of lipid, i.e., 40% (w/v) olive oil, and surfactants, i.e., 20% (w/v) Cremophor RH and 40% (w/v) TWEEN® 85. The third LBF was of type IV and only contained surfactants, i.e., 35% (w/v) Cremophor RH and 67% (w/v) TWEEN® 85. The three LBFs were loaded with fenofibrate. All LBFs were loaded with the same amount of drug (80 mg fenofibrate/g LBF).

Drug-loaded LBFs (1.5 g) were dispersed in the donor solution for 10 min (time −10 min until time 0 min) before digestion was initiated (at time 0 min) by adding recombinant lipase immobilized on polymer beads (Novozyme 435®; 750 mg). The lipid digestion resulted in the liberation of FFAs, which caused a drop in pH. The pH drop was compensated for by equimolar addition of NaOH by the autoburette. The digestion experiments were run for 90 min unless prematurely terminated due to membrane damages, as indicated below. Samples were taken from both chambers to (i) determine drug distribution in the aqueous phase of the digestion medium and (ii) determine mass transfer of the drug across the absorption membrane.

A standard experiment is performed for 90 minutes. Any damages to the membrane will result in an increase of the pH in the donor chamber due to mixing of the donor solution and the absorption solution. Such a pH increase is used as an in situ marker of damaged absorption membrane and indicates at which time point the experiment has to be terminated.

Digestion of the drug-loaded LBFs was performed in the in vitro intestinal drug disposition device and the percentage of fenofibrate in the aqueous phase was compared to literature data obtained with the standard protocol in a single-chamber digestion vessel that did not include an absorption membrane separating a donor chamber and a receiver chamber.

Results

Figure 8:
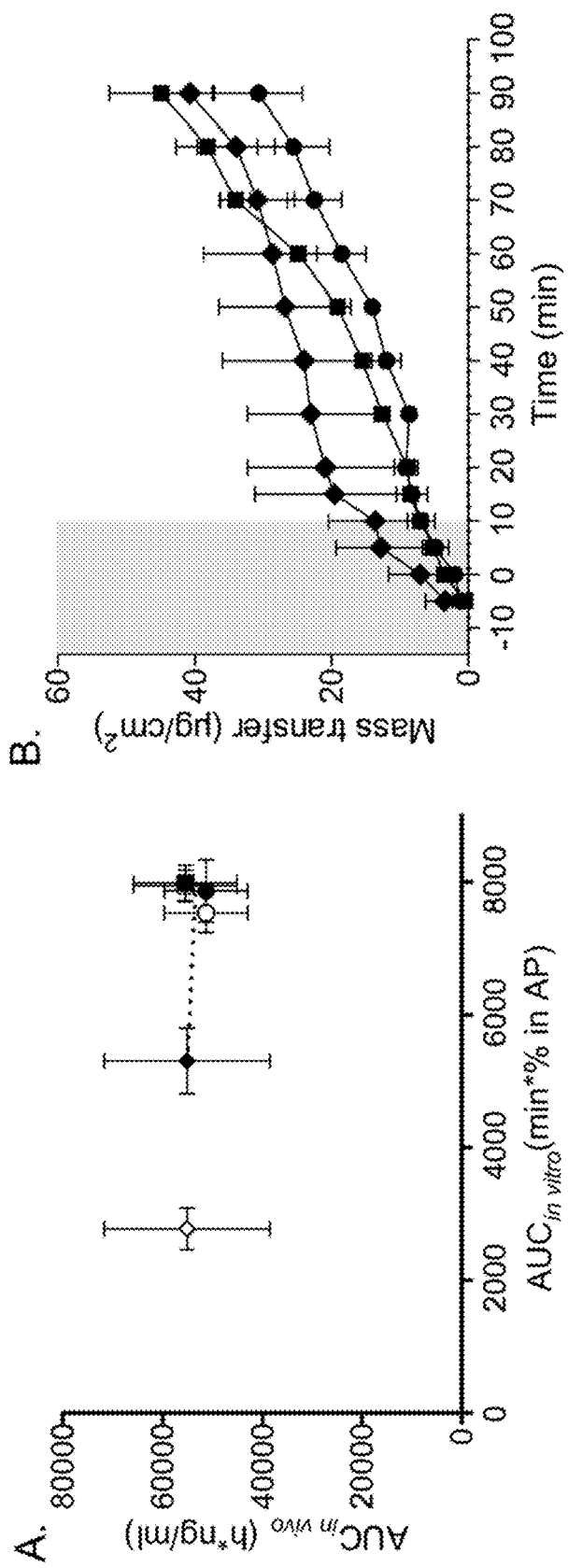
FIG. 8A is a diagram illustrating in vitro-in vivo correlation of in vivo plasma exposure and fenofibrate distribution to the aqueous phase in the donor chamber of the in vitro intestinal drug disposition device during dispersion and digestion. Squares, circles and diamonds represent results for a type IIIA medium chain (IIIA-MC), a type IIIA long chain (IIIA-LC) and a type IV (IV) formulation, respectively. The open symbols represent the data produced by Griffin et al. [6]. Values are expressed as average values±SD (n=3).
FIG. 8B is a diagram illustrating fenofibrate transfer across monolayers to the receiver chamber during dispersion (grey shaded area) and digestion (white area) in the in vitro intestinal drug disposition device. Values are expressed as average values±SD (n=3).
FIG. 8C is a diagram illustrating in vitro in vivo correlation of in vivo plasma exposure and fenofibrate transfer across monolayers to the receiver chamber during dispersion and digestion. Values are expressed as average values±SD (n=3).
Figure 8:
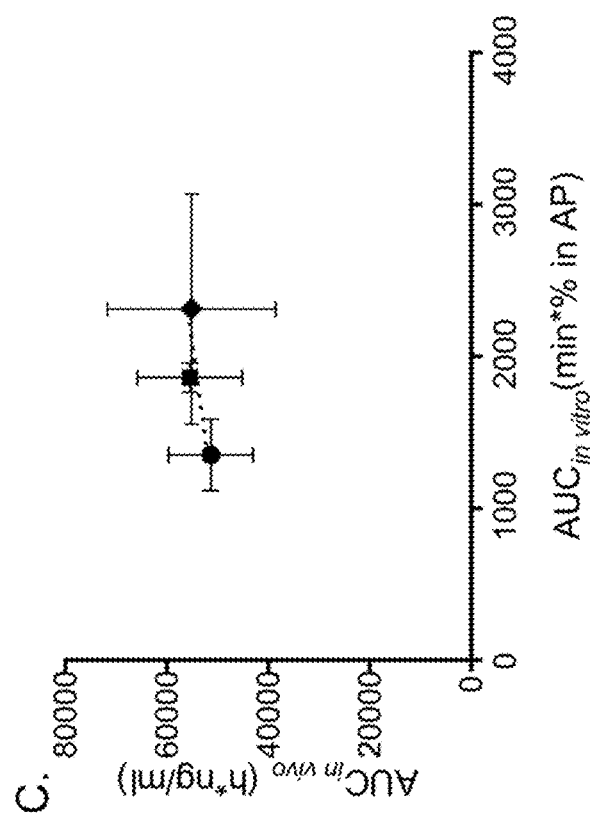

In agreement with findings in the previous study, aqueous concentrations in the digestion chamber predicted significantly higher exposure upon administration of a type IIIA medium chain and IIIA long chain formulation than upon administration of the type IV formulation (FIG. 8A). However, mass transfer of fenofibrate was similar for the three formulations (FIG. 8B), predicting similar in vivo exposure of fenofibrate after administration of IIIA medium chain, IIIA long-chain and IV (FIG. 8C).

Experiment 4

The donor chamber of the in vitro intestinal drug disposition device in Experiment 1 and 2 was cone shaped in order to optimize the absorption-surface-area-to-donor-volume ratio (A/V), while reaching sufficiently high levels of digestion medium that allowed pH measurements and titration. Currently available in vitro methods combing dissolution/release and permeation studies (i) provide small A/V-values (0.04-0.22 $cm^{-1}$) and (ii) do not allow evaluation of complex intestinal processes including digestion [7-9]. The A/V (0.47 $cm^{-1}$) in the in vitro intestinal drug disposition device in Experiment 1 and 2 was high and enabled the measurement of the extent of digestion as well as mass transfer while maintaining sink conditions. The current volume in the donor chamber (60 ml) was initially selected to obtain donor-volume-to-receiver-volume ratio of 1:3, which is commonly used in permeation studies [10]. However, this volume can be decreased to 20 mL, which would result in A/V of 1.41 $cm^{-1}$, which more closely reflects the human small intestine (1.9-2.3 $cm^{-1}$) [11].

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

REFERENCES

[1] *Pharmaceutical Research* 2014, 31(12): 3426-3444

[2] *Pharmaceutical Research* 2016, 33(4): 970-982

[3] *European Journal of Pharmaceutics and Biopharmaceutics* 2007, 67: 96-105

[4] *Journal of Pharmaceutical Sciences* 2012, 101(9): 3360-3380

[5] *Advanced Drug Delivery Reviews* 2016, 101: 167-194

[6] *European Journal of Pharmaceutics and Biopharmaceutics* 2014, 86(3): 427-437

[7] *Pharmaceutical Research* 2003, 20(10): 1674-1680

[8] *Journal of Pharmacy and Pharmacology* 2005, 57(12): 1565-1573

[9] Tsinman and Tsinman, Degree and Extent of Supersaturation of amorphous Pharmaceuticals and Their Flux through Lipophilic Membranes, 2016 AAPS Annual Meeting & Exposition, Nov. 13-17, 2016, Denver, Colo., U.S. (http://abstracts.aaps.orgNerify/AAPS2016/PosterSubmissions/34W0300.pdf)

[10] *Nature Protocols* 2007 2(9): 2111-2119

[11] *Biopharmaceutics and Drug Disposition* 2012, 33(7): 378-402

[12] *AAPS PharmSciTech* 2016, 17(3): 553-571

The invention claimed is:

1. An in vitro intestinal drug disposition device comprising:
    a donor chamber configured to contain a donor solution and having a bottom end and a top end;
    a receiver chamber configured to contain an absorption solution; and
    an absorption membrane arranged in between and separating said donor chamber and said receiver chamber, wherein
    a first main side of said absorption membrane is configured to be in contact with said donor solution and a second, opposite main side of said absorption membrane is configured to be in contact with said absorption solution;
    a ratio of an internal volume of said donor chamber to an area of said first main side of said absorption membrane is equal to or smaller than 3 ml/cm$^2$; and
    a cross-sectional area of said donor chamber at said bottom end is larger than a cross-sectional area of said donor chamber at said top end.

2. The in vitro intestinal drug disposition device according to claim 1, wherein said ratio of said internal volume of said donor chamber to said area of said first main side of said absorption membrane is equal to or smaller than 2.5 ml/cm$^2$.

3. The in vitro intestinal drug disposition device according to claim 2, wherein said ratio of said internal volume of said donor chamber to said area of said first main side of said absorption membrane is equal to or smaller than 2.25 ml/cm$^2$.

4. The in vitro intestinal drug disposition device according to claim 3, wherein said ratio of said internal volume of said donor chamber to said area of said first main side of said absorption membrane is equal to or smaller than 2 ml/cm$^2$.

5. The in vitro intestinal drug disposition device according to claim 1, wherein a ratio of said internal volume of said donor chamber to an internal volume of said receiver chamber is smaller than 1.

6. The in vitro intestinal drug disposition device according to claim 5, wherein the ratio of said internal volume of said donor chamber to an internal volume of said receiver chamber is equal to or smaller than ½.

7. The in vitro intestinal drug disposition device according to claim 6, wherein the ratio of said internal volume of said donor chamber to an internal volume of said receiver chamber is equal to or smaller than ⅓.

8. The in vitro intestinal drug disposition device according to claim 1, wherein a cross-sectional area of said donor chamber is continuously or step-by-step decreasing from said bottom end towards said top end.

9. The in vitro intestinal drug disposition device according to claim 1, wherein
    said donor chamber is a cone-shaped donor chamber; and
    said receiver chamber is a cylinder-shaped receiver chamber.

10. The in vitro intestinal drug disposition device according to claim 1, wherein
    said donor chamber comprises a first fluid jacket configured to contain a fluid having a temperature within a first temperature range; and
    said receiver chamber comprises a second fluid jacket configured to contain a fluid having a temperature within a second temperature range.

11. The in vitro intestinal drug disposition device according to claim 1, wherein said absorption membrane is a semipermeable membrane comprising a cell layer on said first main side of said absorption membrane.

12. A system for in vitro intestinal drug disposition comprising:
    an in vitro intestinal drug disposition device according to claim 11, wherein
    said receiver chamber comprises a sampling port configured to provide access to an internal volume of said receiver chamber; and
    said in vitro intestinal drug disposition device comprises a chamber lid for said donor chamber, said chamber lid comprises a sampling port configured to provide access to said internal volume of said donor chamber; and
    an analysis device comprising an analysis probe arranged in an opening in said chamber lid.

13. The system according to claim 12, wherein said analysis device is a pH meter configured to measure a pH of said donor solution, said system further comprising a dispensing device configured to dispense a pH adjusting agent into said donor solution in response to a pH change of said donor solution measured by said pH meter.

14. An in vitro intestinal drug disposition method comprising:
    adding a test substance to said donor chamber of an in vitro intestinal drug disposition device according to claim 1, wherein
    said donor chamber contains a donor solution; and
    said receiver chamber contains an absorption solution; and
    determining concentration of said test substance and/or a digestion metabolite of said test substance in at least one of said donor solution and said absorption solution at at least one time instance.

* * * * *